(12) United States Patent
Suwito

(10) Patent No.: US 9,511,216 B2
(45) Date of Patent: Dec. 6, 2016

(54) MODULAR BIOMEDICAL IMPLANTS

(75) Inventor: Wantjinarjo Suwito, Longmont, CO (US)

(73) Assignee: ADVANCED BIONICS AG, Staefa (CH)

( * ) Notice: Subject to any disclaimer, the term of this patent is extended or adjusted under 35 U.S.C. 154(b) by 43 days.

(21) Appl. No.: 14/345,366

(22) PCT Filed: Sep. 28, 2011

(86) PCT No.: PCT/US2011/053742
§ 371 (c)(1),
(2), (4) Date: Mar. 17, 2014

(87) PCT Pub. No.: WO2013/048396
PCT Pub. Date: Apr. 4, 2013

(65) Prior Publication Data
US 2014/0350652 A1 Nov. 27, 2014

(51) Int. Cl.
| | |
|---|---|
| *A61N 1/05* | (2006.01) |
| *A61N 1/36* | (2006.01) |
| *H01R 13/24* | (2006.01) |
| *A61N 1/375* | (2006.01) |
| *A61N 1/372* | (2006.01) |
| *H01R 13/52* | (2006.01) |
| *H01R 13/622* | (2006.01) |

(52) U.S. Cl.
CPC .............. *A61N 1/05* (2013.01); *A61N 1/0541* (2013.01); *A61N 1/36032* (2013.01); *A61N 1/372* (2013.01); *A61N 1/3752* (2013.01); *H01R 13/2414* (2013.01); *H01R 13/5224* (2013.01); *H01R 13/622* (2013.01); *H01R 2201/12* (2013.01)

(58) Field of Classification Search
CPC ........ A61N 1/372; A61N 1/05; A61N 1/0541; A61H 39/002
USPC .......................................... 607/136–137, 116
See application file for complete search history.

(56) References Cited

U.S. PATENT DOCUMENTS

| | | |
|---|---|---|
| 3,867,932 A | 2/1975 | Huene |
| 4,142,532 A | 3/1979 | Ware |
| 4,495,917 A | 1/1985 | Byers |
| RE33,170 E * | 2/1990 | Byers ........................ A61F 2/18 128/903 |
| 5,755,743 A | 5/1998 | Volz et al. |
| 5,782,645 A | 7/1998 | Stobie et al. |
| 6,198,969 B1 | 3/2001 | Kuzma |
| 6,233,488 B1 | 5/2001 | Hess |

(Continued)

FOREIGN PATENT DOCUMENTS

GB         2166606 A        5/1986

*Primary Examiner* — Roland Dinga
(74) *Attorney, Agent, or Firm* — Fabian VanCott; Steven Nichols

(57) ABSTRACT

A modular biomedical implant includes a processor, an electrode array, and a cable. The first end of the cable is attached to the electrode array and a second end of the cable terminates in a first array of contacts. A second array of contacts is electrically connected to the processor. A separate anisotropic conductor is disposed between the first array of contacts and the second array of contacts and forms electrical connections between the first array of contacts and the second array of contacts. A method for replacing a processor of a modular biomedical implant is also provided.

9 Claims, 17 Drawing Sheets

(56) References Cited

U.S. PATENT DOCUMENTS

| | | |
|---|---|---|
| 6,321,126 B1 | 11/2001 | Kuzma |
| 6,415,168 B1 | 7/2002 | Putz |
| 7,534,127 B2 | 5/2009 | Parker |
| 7,856,705 B2 | 12/2010 | Degieux et al. |
| 2007/0207569 A1 | 9/2007 | Greenberg et al. |
| 2008/0177297 A1 | 7/2008 | Steiner et al. |
| 2009/0177239 A1 | 7/2009 | Castro |
| 2009/0240314 A1 | 9/2009 | Kong |
| 2011/0196446 A1 | 8/2011 | Wu et al. |

* cited by examiner

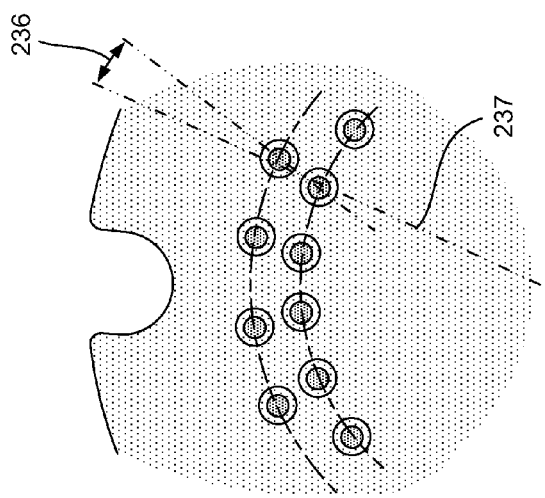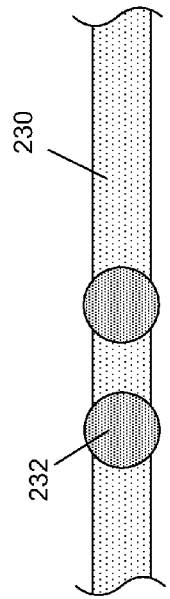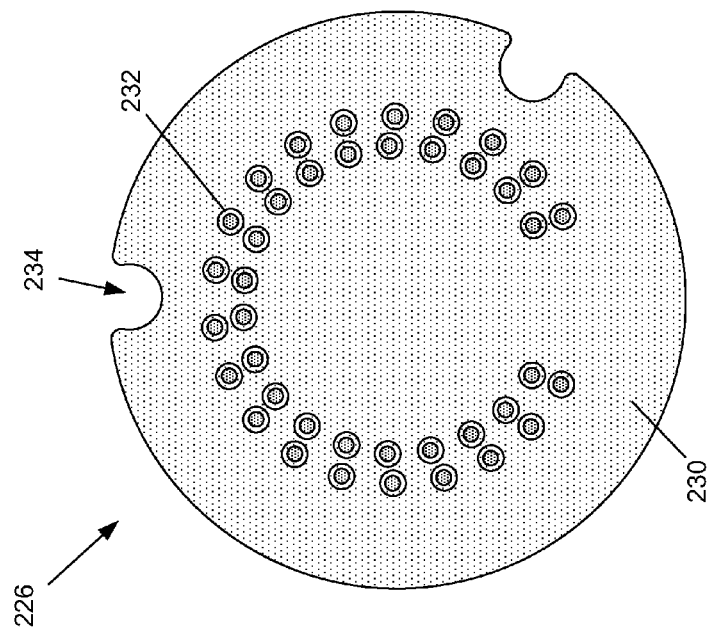
Fig. 5B
Fig. 5C
Fig. 5A

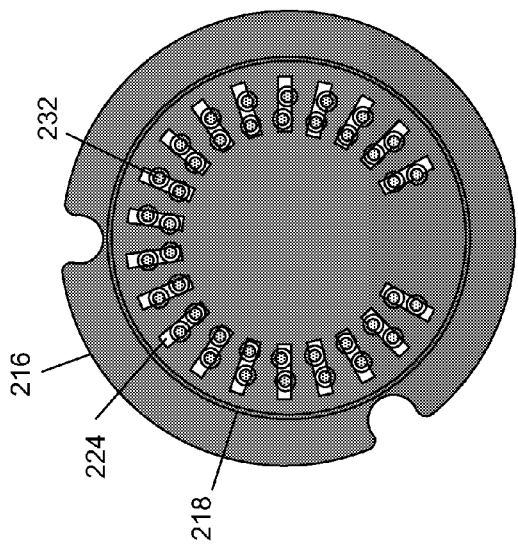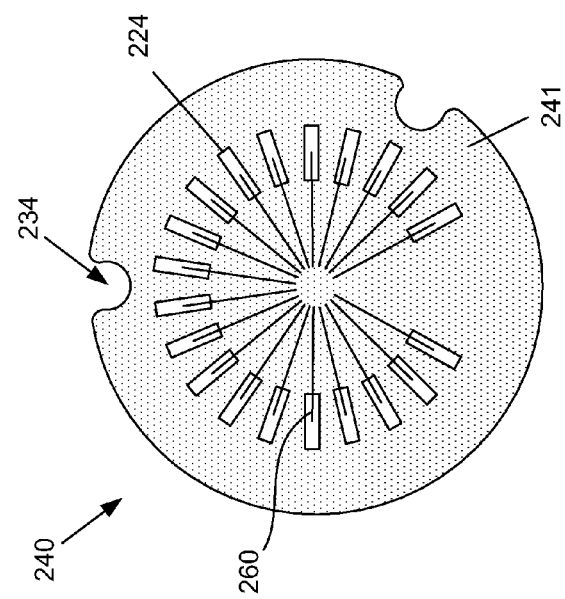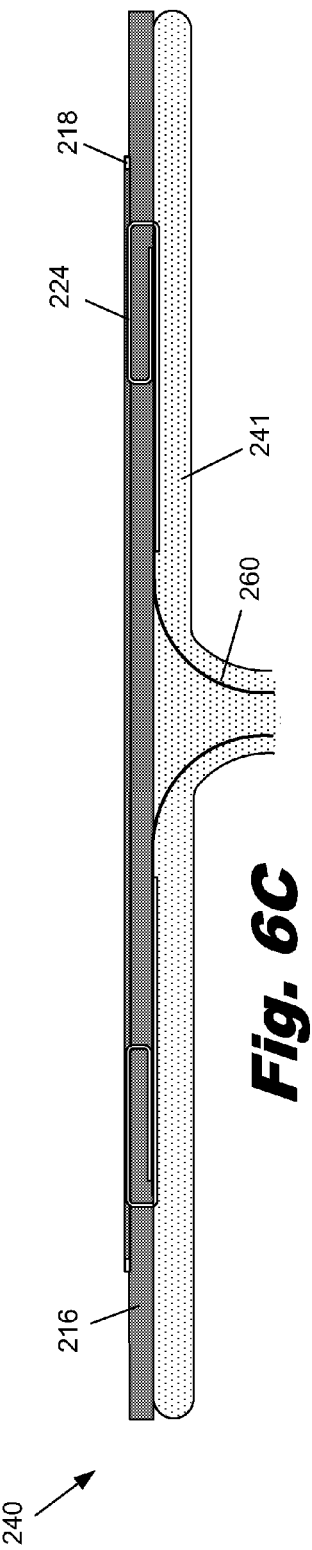

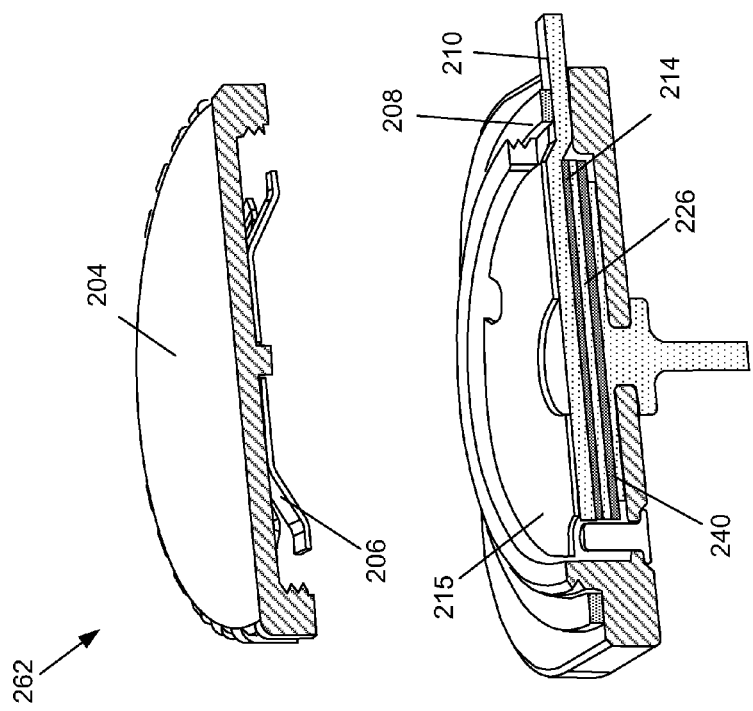
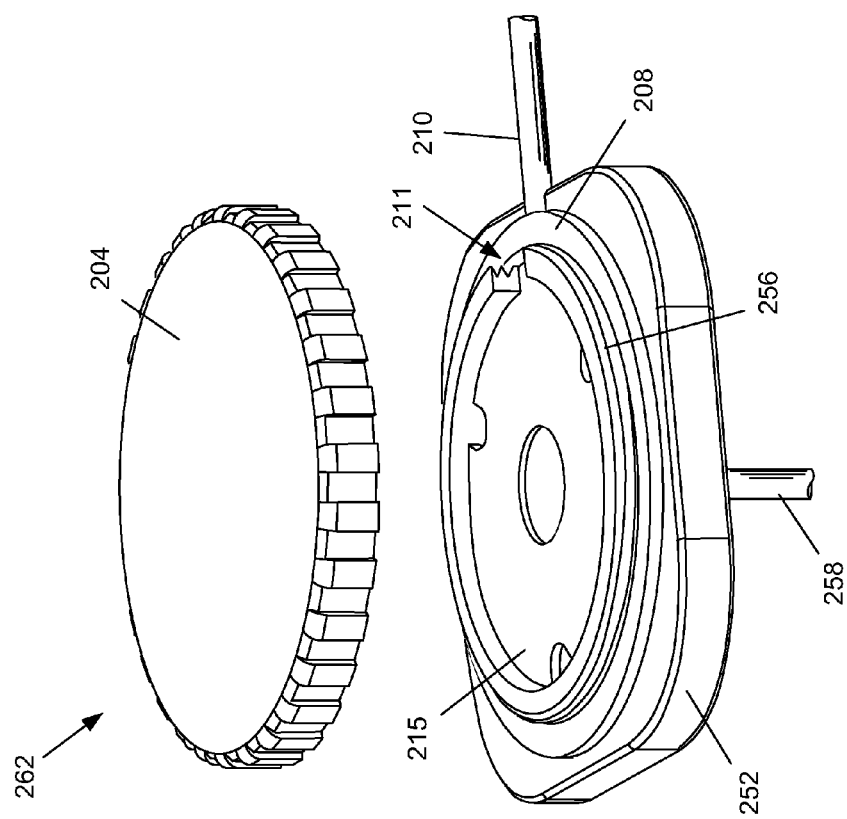
Fig. 9
Fig. 8

MODULAR BIOMEDICAL IMPLANTS

BACKGROUND

Long term biomedical implants can support the functions of the human body to sustain life and significantly improve quality of life. For example, active biomedical implants can provide nerve stimulation to maintain or improve biological functions. Examples of active biomedical implants include pacemakers, brain implants, retinal prosthesis, and cochlear implants. Active biomedical implants typically include a processor that generates signals, an electrode or electrode array located in proximity to nerve tissue, and a cable that electrically connects the processor to the electrode array. Patients often rely on these active implants throughout their lifetime.

Replacement or repair of biomedical implants can be problematic. Over the 80+ year life span of a human, significant improvement in electronics can be expected. This can lead to a desire to replace the processor for improved reliability, increased function, and lower power consumption. Additionally, the electronics within the processor may be compromised by impacts, accidents, chemical corrosion, and vapor ingress. Currently, in many cases, replacing the processor requires explanting the attached electrodes. Explanting electrodes can cause damage to the adjacent nerve tissues and structures. Further, there is no guarantee that the replacement electrodes can be placed in the same location as the previous electrodes.

BRIEF DESCRIPTION OF THE DRAWINGS

The accompanying drawings illustrate various examples of the principles described herein and are a part of the specification. The illustrated examples are merely examples and do not limit the scope of the claims.

FIGS. 5A-5C are views of an illustrative anisotropic conductor, according to one example of principles described herein.

FIGS. 6A-6C are views of an illustrative contact plate, according to one example of principles described herein.

FIG. 8 is a perspective view of a 90 degree inline connector, according to one example of principles described herein.

FIG. 9 is a cutaway perspective view of a 90 degree inline connector, according to one example of principles described herein.

Throughout the drawings, identical reference numbers designate similar, but not necessarily identical, elements.

DETAILED DESCRIPTION

Figure 1:
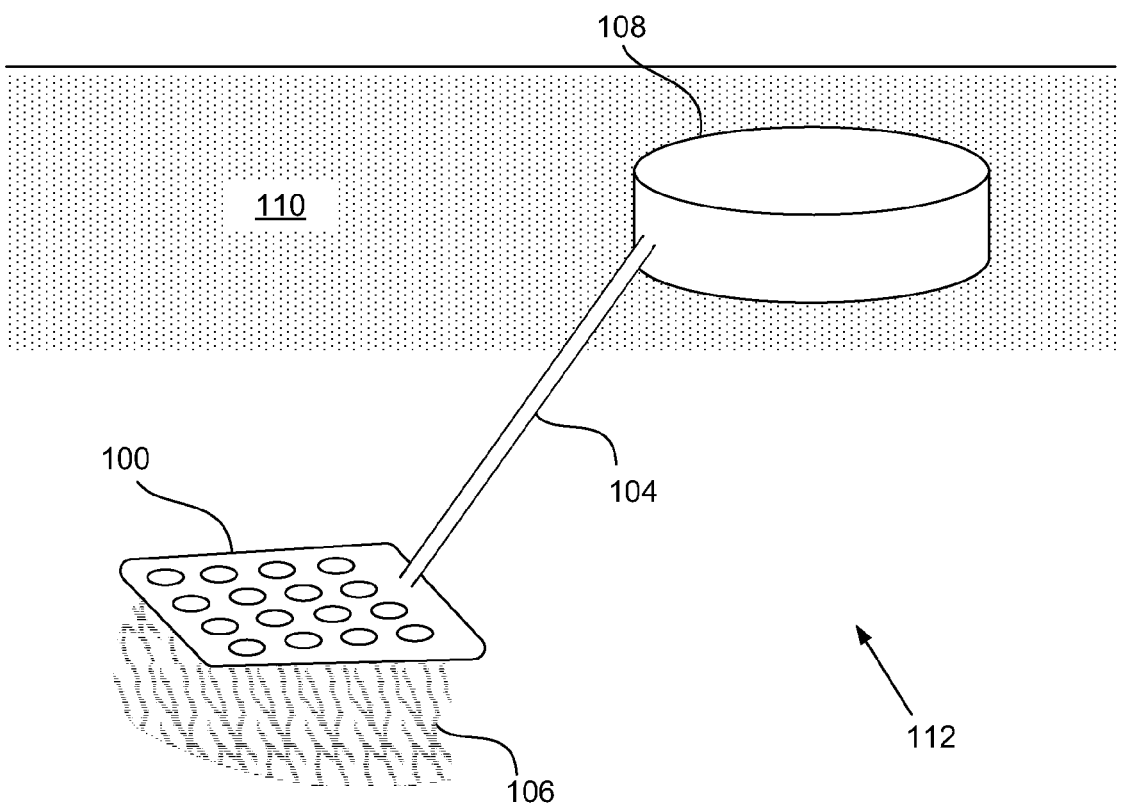
FIG. 1 is a diagram of an illustrative biomedical implant, according to one example of principles described herein.

Active biomedical implants typically include an implanted processor that generates signals, an electrode or electrode array located in proximity to nerve tissue, and a cable that electrically connects the processor to the electrode array. Patients often rely on these implants throughout their lifetime. The processor is typically the most complex component in the implant and is the most vulnerable to failure from impacts, accidents, chemical corrosion, and vapor ingress. Further, over the 80+ year life span of a human, significant improvement in electronics can be expected. This can lead to a desire to replace the processor for improved reliability, increased function, and lower power consumption. In many instances replacing the processor also requires explanting the attached electrodes. Explanting electrodes can cause damage to the adjacent nerve tissues and structures. Further, there is no guarantee that the replacement electrodes can be placed in the same location as the previous electrodes. When the electrodes of the new electrode array do not stimulate the same nerves as the explanted electrode array, the patient may lose function and/or have to "relearn" how to interpret the output of the electrode array. Consequently, it is desirable for the implant to be designed so that the processor can be replaced without disturbing the electrode array.

Principles, systems, and methods for modular biomedical implants are described below. The illustrative modular biomedical implants allow for explantation of the processor electronics without disturbing the electrode array or nerve tissues adjacent to the electrode array. Connectors that are inline with cable connecting the processor and electrode array are described. These connectors allow the cable to be separated into two separate parts. One part is connected to the processor and a second part is connected to the electrode array. To replace the processor, the inline connector is disconnected. The processor and the portion of the cable attached to the processor are removed and replaced with a new processor and a new cable. The new processor cable is then connected to the cable attached to the electrode array using the inline connector.

In other embodiments described below the processor is retained within a case. The case can be opened, the processor removed, and a replacement processor placed into the case. A number of illustrative surgical tools are described to facilitate the opening of the case or inline connector and replacing the processor.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that one example, but not necessarily in other examples.

FIG. 1 is a diagram of a biomedical implant (112) that includes an implanted processor (108), an imbedded electrode array (100) and a cable (104) connecting the processor (108) to the electrode array (100). The implanted processor (108) is located directly under the skin (110). Both the implanted electrode array (100) and implanted processor (108) are hardwired to the cable (104). Thus, to replace the implanted processor (108), the entire device must be explanted and a new device implanted. As discussed above, this can disturb sensitive nerve tissue (106) surrounding the imbedded electrode array (100). The nerves (106) and connective tissue may grow into or around the electrode array (100). Explantation of the electrode array (100) may tear these nerves (106) and connective tissue, resulting in a loss of function and inflammation. Further, when the new electrode array is implanted, it may not be positioned precisely in the same location as the previous electrode array. Consequently, the patient may have to relearn how to accept and process stimuli presented by the new electrode array through a different combination of nerves.

Figure 2:
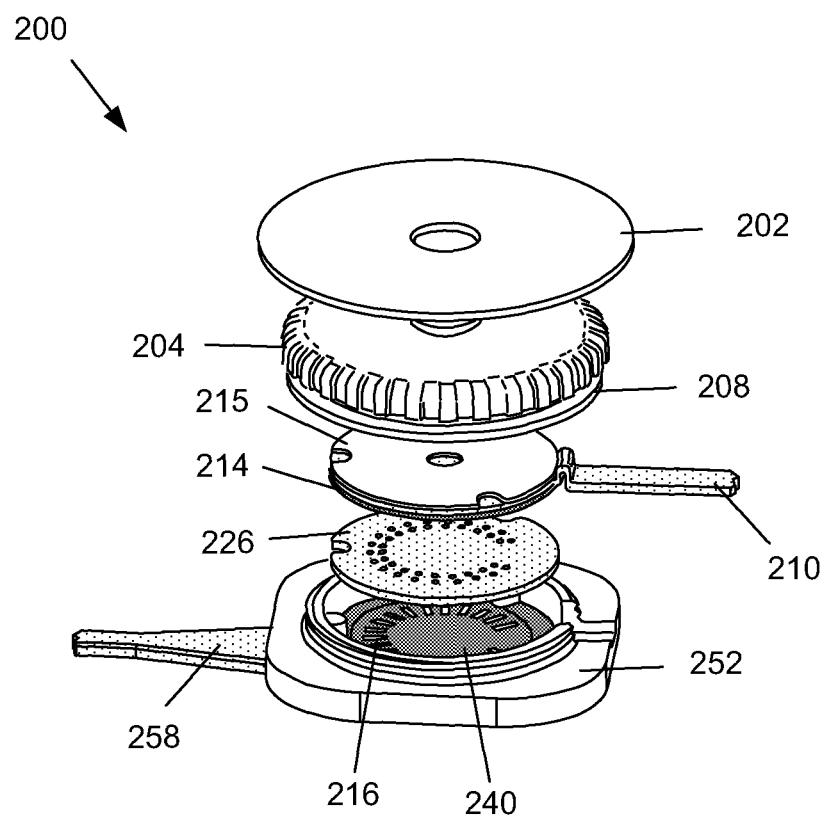
FIG. 2 is an exploded perspective view of an inline connector, according to one example of principles described herein.

FIG. 2 is an exploded perspective view of an illustrative inline connector (200) that can be positioned in the cable (104, FIG. 1) connecting the processor (108, FIG. 1) and the electrode array (100, FIG. 1). The inline connector (200) allows the cable (104, FIG. 1) to be separated into two portions, with a first portion (258) of the cable attached to the electrode array (100, FIG. 1) and a second portion (210) of the cable attached to the processor (108, FIG. 1). The processor (108, FIG. 1) and its attached cable portion (210) can be replaced without disturbing the electrode array (100, FIG. 1) by disconnecting the inline connector (200). A new processor and cable portion can be attached to the electrode array (100, FIG. 1) using the inline connector (200).

The inline connector (200) includes a base (252), a lower contact plate (240), and a first portion of the cable (258) that connects to the electrode array. The electrical conductors in first portion of the cable (258) are electrically connected to the array of contacts (216) on the lower contact plate (240). An upper contact plate (214) includes a second array of contacts that are electrically connected to a second portion (210) of the cable connected to the processor.

An anisotropic conductor (226) is sandwiched between the upper contact plate (214) and the lower contact plate (240). The anisotropic conductor (226) is configured to conduct electricity through its thickness but not to conduct electricity horizontally. This allows the array of contacts on the upper contact plate (214) to be electrically connected to the array of contacts (216) on the lower contact plate (240) without undesirable lateral shorting between contacts. In one application, the anisotropic conductor (226) may include a deformable matrix embedded with deformable conductors.

The upper contact plate (214), anisotropic conductor (226), and lower contact plate (240) are pressed together by a cap (204) that screws onto the base (252). The matrix and conductors in the anisotropic conductor (226) may elastically and/or plastically deform under the applied pressure. In some embodiments, the cap (204) may press against a pressure plate (215) to apply uniform pressure on each contact. The outer rim of the cap (204) may sandwich a gasket (208) against the upper surface of the base (252). This gasket (208) creates a water and vapor barrier to prevent undesirable intrusion of contaminants into the connector (200). An overcoat (202) can be deposited over the cap (204) to prevent abrasion of the skin and tissues that overlie the cap (204). In some embodiments, the overcoat (202) may be a toroidal disk that allows for tissue in-growth below the overcoat (202). This in-growth can secure the cap (204) in place and prevent the cap (204) from unscrewing over time. The tissue in-growth can be easily removed during revision surgery.

Figure 3:
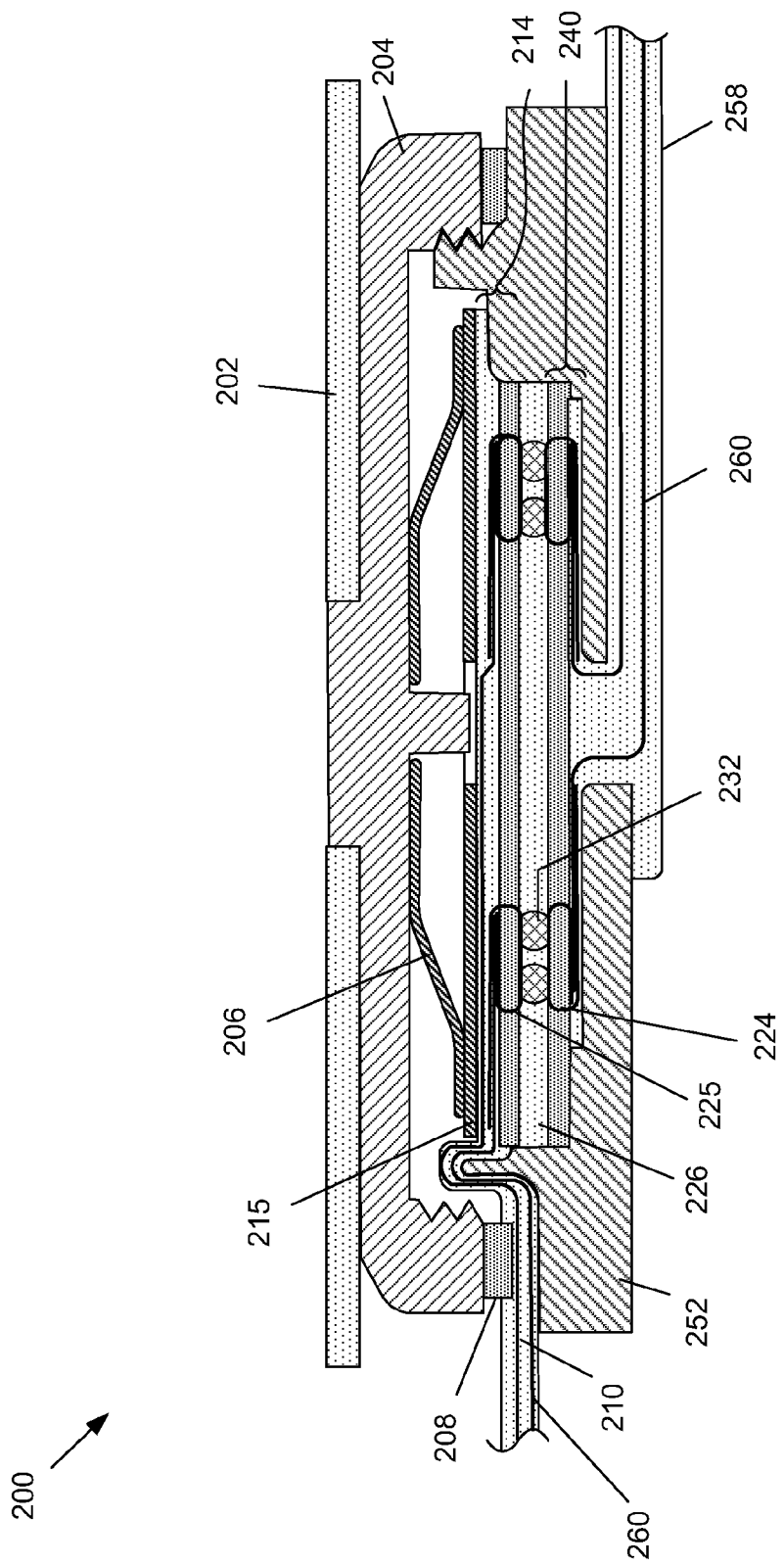
FIG. 3 is a cross sectional view of the inline connector shown in FIG. 2, according to one example of principles described herein.

FIG. 3 is a cross sectional view of the inline connector (200). The base (252) of the inline connector (200) has a cavity that accepts the lower contact plate (240), the anisotropic conductor (226), and the upper contact plate (214). The base (252) includes cutouts to provide for routing of the cables (210, 258) into the base. The base (252) may be formed from any of a variety of biocompatible materials, including titanium, stainless steel and medical grade polymers. In this embodiment, the anisotropic conductor (226) is formed from an elastomer with embedded conductive balls (232). Upper and lower contact plates (214, 240) are disposed on the terminal ends of the first and second portions of the cable (210, 258) that connect to the processor and the electrode array, respectively. In the upper and lower contact plates (214, 240), the signal wires (260) are routed to the contacts (224, 225).

In this implementation, a spring (206) located in the cap (204) presses against a pressure plate (215) to provide the desired level of compression force. The pressure plate (215) distributes the spring pressure over the top surface of the upper contact plate (214). This compression forces presses the contacts (224, 225) against the conductive balls (232) in the anisotropic conductor (226). The conductive balls (232) are made from softer material than the contacts (224) and deform when pressed between an upper contact (225) and lower contact (224).

As discussed above, a gasket (208) is placed under the outer lip of the cap (204). As the cap (204) is tightened, the gasket (208) is compressed and provides a seal that helps prevent intrusion of biological fluids and vapors into the interior of the inline connector (200).

FIGS. 4A-F are top views of an inline connector (200) showing an illustrative assembly sequence. In a first step shown in FIG. 4A, the lower contact plate (240) is secured in place in the base (252) with the lower contacts (224) facing upward and the cable (258) to the electrode array exiting the base (252). The lower contact plate (240) may not be configured for removal from the base (252) once it is installed because the electrode array (100, FIG. 1) typically remains in place. If electrode array (100, FIG. 1) is removed, the entire inline connector (200) can be removed with it. Consequently, the lower contact plate (240) may be molded, glued, or otherwise sealed into place to ensure that there is minimal leakage into the connector (240).

Figure 4C:
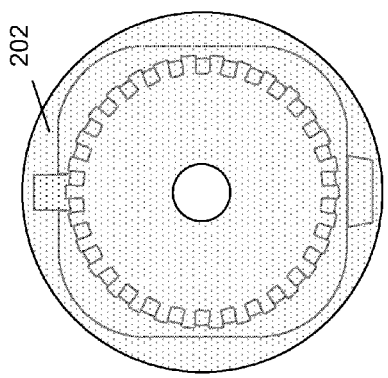
FIGS. 4A-F are top views of an inline connector showing an illustrative assembly sequence, according to one example of principles described herein.
Figure 4F:
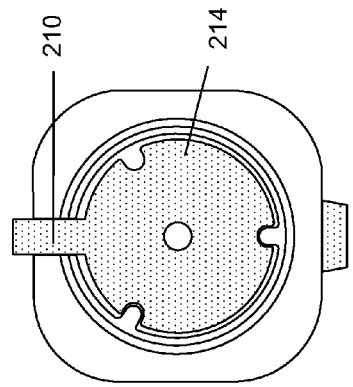
Figure 4B:
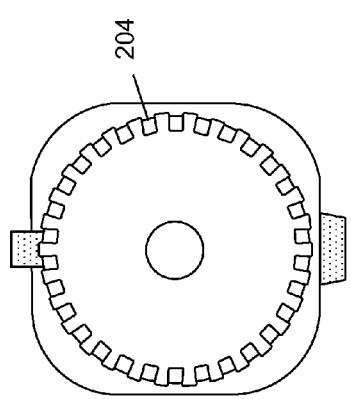

FIG. 4B shows an anisotropic conductor (226) that has been disposed in the cavity of base (252) over the lower contacts (224). In this embodiment, the anisotropic conductor (226) includes an elastomeric matrix (230) with a number of embedded balls (232). In other implementations the anisotropic conductor (226) may have other features, such as conductive strands oriented through the thickness of the anisotropic conductor (226).

FIG. 4C shows the upper contact plate (214) placed over the anisotropic conductor (226), with the contacts (224) on the upper contact plate (214) facing downward. The upper contact plate (214) is connected to the cable (210) that connects to the processor. The upper surface of the upper contact plate (214) is formed from a biocompatible polymer encapsulant, such as silicone, that protects the underlying signal wires.

Figure 4E:
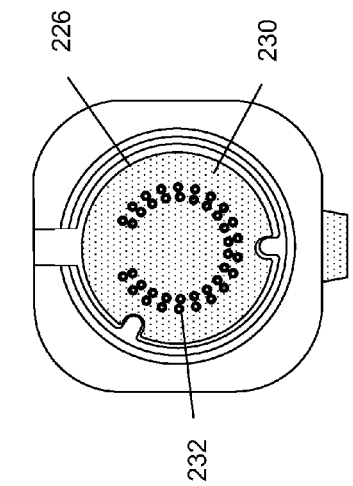
Figure 4A:
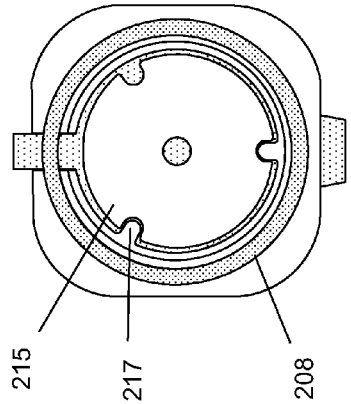
Figure 4D:
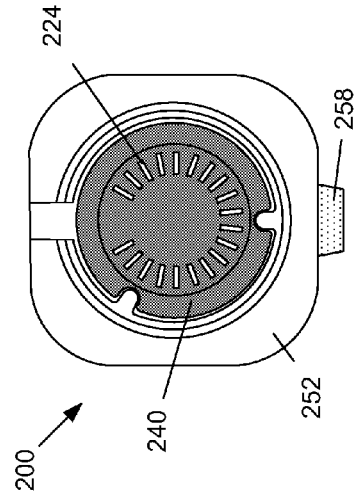

FIG. 4D shows a pressure plate (215) placed over the upper contact plate (214). Alignment features (217) are used to maintain the alignment of the various plates during the assembly process. Each of the contact plates (214, 240) has a notch or hole corresponding to the alignment features (217). A gasket (208) is placed on the base (252) around the exterior of the cavity. FIG. 4E shows a cap (204) screwed onto the threads on the base (252). As discussed above, the cap (252) compresses the gasket (208) against the base (252). FIG. 4F shows the overcoat (202) placed over the top of the cap (204).

To replace an old processor, the steps shown in FIGS. 4B-4F are reversed to remove the old processor and then performed in sequence to connect a new processor to the electrode array. The components that were removed from the inline connector (such as the anisotropic conductor, pressure plate, cap, and overcoat) may be replaced with new components as necessary.

FIGS. 5A-5C are views of an illustrative anisotropic conductor (226). In the implementation shown in FIG. 5A, the anisotropic conductor (226) includes an elastomeric matrix (230) and two concentric partial rings of conductive balls (232). The anisotropic conductor (226) also includes alignment cutouts (234) that correspond to alignment features (217, FIG. 4D) in the base (252, FIG. 4A). FIG. 5B shows that the location of the conductive balls (232) around the two concentric rings is staggered so that a pair of two adjacent balls (232) is offset from a radial line (237) by a stagger angle (236). The purpose of the stagger angle (236) is to position the balls (232) to increase the likelihood that at least one of the balls (232) will line up with a pair of opposing contacts. The balls have a diameter that is greater than the thickness of the elastomeric matrix (230) and a portion of the ball (232) extends from either side of the elastomeric matrix (230) as shown FIG. 5C. As discussed above, the balls (232) may be formed from material that deforms after sealing to increase the contact area and conform to the surface profiles of the contacts. This ensures a robust electrical connection between the two electrodes arrays.

FIGS. 6A-6C are views an illustrative lower contact plate (240). FIG. 6A shows a plan view of the lower contact plate (240) from the bottom. The lower contact plate (240) includes an elastomeric encapsulant (241) and signal wires (260) passing through the elastomeric encapsulant (241) to connect with the contacts (224). The alignment cutouts (234) are formed in the edges of the contact plates and anisotropic conductor. Where radial orientation of the component is important, the cutouts can be keyed so that they match the alignment features in only one radial orientation. This ensures proper alignment of the contacts and anisotropic conductor.

FIG. 6B shows a plan view of the lower contact plate (240) from the top. The upper surface of the plate (240) is formed from a substantially impermeable substrate (226) that includes a ridge (218) and contacts (224). In this example, the ridge (218) is a complete circle that encircles the contacts (224). The ridge (218) creates a seal that impedes fluid and gas flow to the contact arrays. This can prevent corrosion of the contacts and disruption of the electrical connections between the contacts. The substantially impermeable substrate (226) can be formed from a variety of biocompatible, electrically insulating materials.

In this example, the contacts (224) are rectangles with their major axis radially aligned with radial lines (237, FIG. 5B) extending outward from the center of the substantially impermeable substrate (226). FIG. 6B also shows an overlay of a number of conductive balls (232) in the anisotropic conductor. The stagger angle (236, FIG. 5B) of the balls (232) makes radial alignment of contacts (224) and anisotropic conductor (226, FIG. 3) less critical and therefore less expensive to manufacture and easier to assemble.

FIG. 6C is a cross sectional view of the lower contact plate (240) that shows the elastomeric encapsulant (241) on the bottom and the substantially impermeable substrate (226) on the top. The contacts (224) are conductive sheets with two legs. The legs pass through the substantially impermeable substrate (226) and then are bent toward each other. Each of the signal wires (260) is each connected to one of the contacts.

Figure 6D:
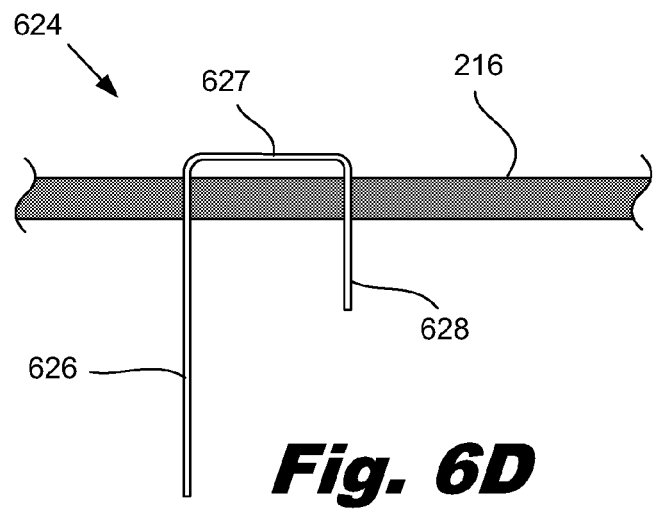
FIGS. 6D-6F are cross sectional views showing the assembly and connection of a contact sheet to a signal wire, according to one example of principles described herein.
Figure 6E:
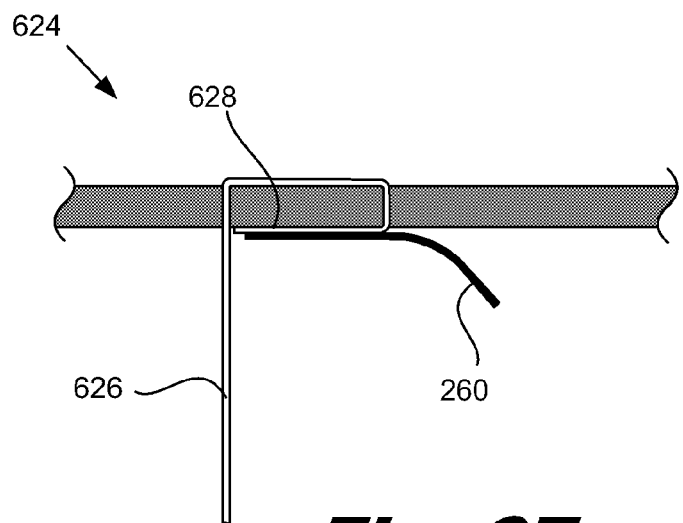
Figure 6F:
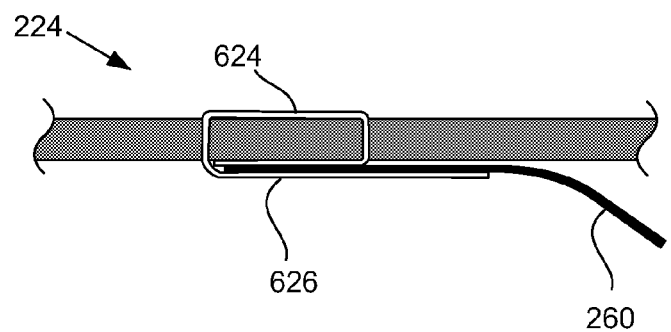

FIGS. 6D-6F are cross sectional views showing the assembly of a contact (224) from a contact sheet (624) and the connection of the contact (224) to a signal wire. In one embodiment, contacts (224) in both the upper and the lower contact plates (214, 240) are formed using this method. In other embodiments, the contacts may be formed using different structures and/or methods.

FIG. 6D shows the contact sheet (624) shaped as an inverted "U" with both legs (626, 628) passing through the substantially impermeable substrate (226). In one example, the contact sheet (624) is a long narrow strip of conductive foil. The foil may be made from a number of materials and have thicknesses ranging from 12.5 to 100 microns. For example, the contact sheet (624) may be formed from platinum iridium foil with a thickness of 50 microns.

FIG. 6E shows a shorter leg (628) of the contact sheet (624) folded toward the longer leg (626) such that the shorter leg (628) lies parallel to the bottom surface of the substantially impermeable substrate (226). The center portion (627) forms the contact surface that is contacted by the anisotropic conductor. The signal wire (260) may attached to the shorter leg (628) by any of a number of methods. For example, the signal wire (260) may be connected by laser welding, soldering, resistance welding, ball bonding, or other appropriate technique.

FIG. 6F shows that the second and longer leg (626) is then bent over the signal wire (260). The second leg (626) of the contact sheet (624) may also be welded or joined to the signal wire (260) and/or the first leg (628). In other embodiments, the second leg (626) may not be directly attached to the signal wire (260) but provides strain relief for the signal wire (260). Following this procedure the contact sheet (624) has been transformed into a contact (224) as shown and illustrated in FIGS. 2-6C.

In summary, the first array of contacts and/or the second array of contacts may be formed from folded metal sheets passing through the substantially impermeable substrate with the signal wires connected to the folded metal sheets on a first surface of the substantially impermeable substrate and the anisotropic conductor being pressed against the folded metal sheets on a second opposing surface of the substantially impermeable substrate. The folded metal sheet has a first leg, a second leg, and a center portion. The first leg and second leg pass through a substantially impermeable substrate such that the center portion is parallel to and directly contacts a first surface of the substantially impermeable substrate. The center portion is the contact pad that is in electrical contact with the anisotropic conductor. The legs are folded parallel to the surface of the substantially impermeable membrane and the signal wire is electrically connected to the at least one of the legs.

Contacts formed using the principles described above may have a number of advantages. The folded metal sheets make a secure connection to both the substrate and the wire and form an electrical contact surface. Further, the resulting contact plates are exceptionally thin. For example, the lower contact plate may have a total thickness between 0.1 and 3.0 millimeters. These exceptionally thin contact plates allow for the inline connector to have a thickness of only 1 to 4 millimeters.

Figure 7:
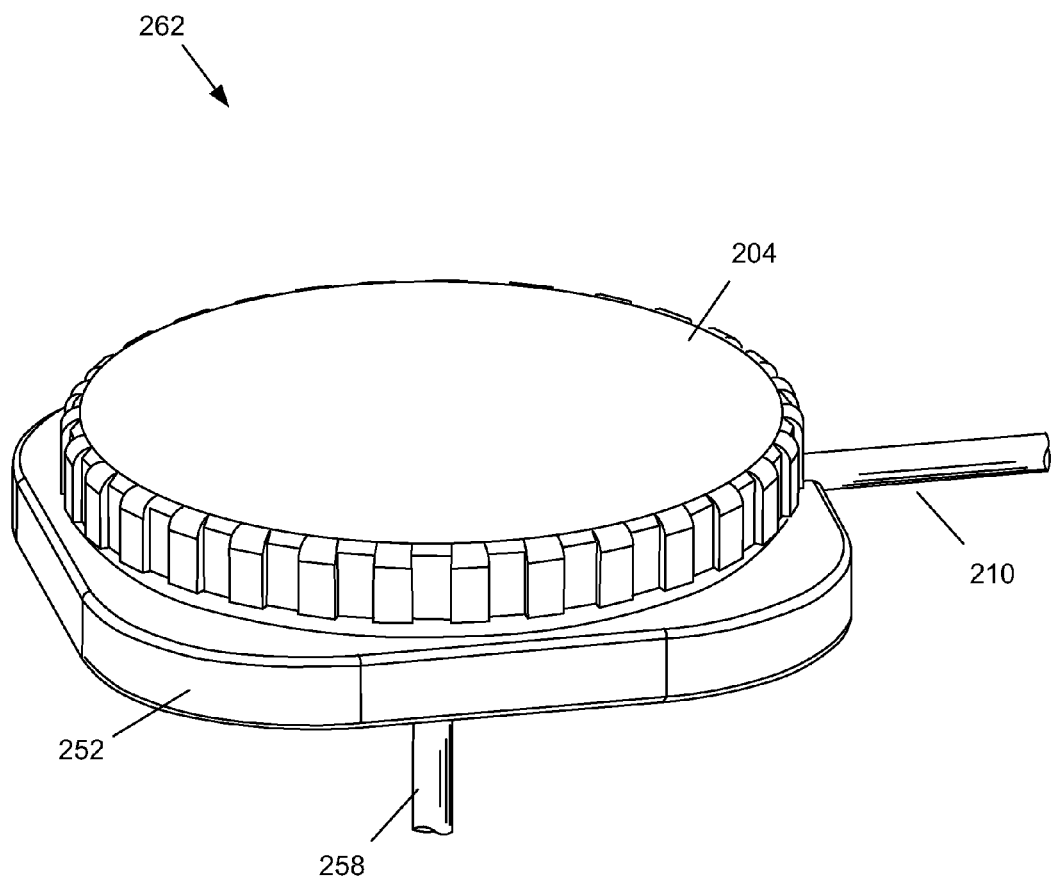
FIG. 7 is a perspective view of a 90 degree inline connector, according to one example of principles described herein.

FIG. 7 is a perspective view of a 90 degree inline connector (262). The 90 degree inline connector (262) includes a horizontal cable (210) from the processor and a vertical cable to the electrode array (258). This configuration can be advantageous when the processor (108, FIG. 1) is located nearer to the skin and the electrode array (100, FIG. 1) is deeper within the tissue. For example, a processor for a brain implant may be placed just under the skin while the electrode array on the brain stem. Similarly, the processor for a retinal or cochlear implant may be beneath the skin and the electrode array is located deeper within the tissue to simulate visual or auditory nerves. The 90 degree inline connector (262) facilitates the routing of the cable into the deeper tissues.

FIGS. 8 and 9 are perspective views of the 90 degree inline connector (262) shown in FIG. 7. FIG. 8 is an exploded view that shows the base (252), cap (204), gasket (208), and pressure plate (215). The upper contact plate, lower contact plate, and anisotropic conductor are located beneath the pressure plate (215). As discussed above, when the cap (204) is screwed onto the outside thread (256) of the base (252), it sandwiches the gasket (208) between the cap (204) and the base (252) to form a seal. In this example, the outside thread (256) is interrupted by an opening (211) for the cable (210) to the processor to pass out of the base cavity.

FIG. 9 is a cross sectional view of the 90 degree inline connector (262). As discussed above, a spring (206) in the cap (204) presses on the pressure plate (215). The pressure plate (215) then compresses the upper contact plate (214), the anisotropic conductor (226), and the lower pressure plate (240) to form reliable electrical interconnections between them. The gasket (208) intersects the cable (210) to the processor and slightly compresses the cable (258) when the cap (204) is tightened. The cable (258) then forms a seal in the opening in the base (252).

To disconnect and replace the processor (108, FIG. 1), the cap (204) is screwed off and the pressure plate (215) is removed. The upper contact plate (214) is also removed. This frees the cable (210) to the processor and the processor (108, FIG. 1) can then be explanted. The anisotropic conductor (226) is also removed. Because the anisotropic conductor (226) deforms when the cap (204) is tightened, it can be desirable to replace it with a new anisotropic conductor (226). Any body fluids that are present in the connector (262) can be removed prior to reassembly of the inline connector (262).

The new anisotropic conductor and new upper contact plate (with its accompanying new processor) are positioned in the base (252) using the alignment features (217, FIG. 4D). The pressure plate (215) is placed over the upper contact plate (214). As the cap (204) is screwed over the outside threads (256), the gasket (208) and the spring (206) are compressed. The gasket (208) forms a seal around the perimeter of the cap (204) and the spring (206) compresses the contact plates and new anisotropic conductor. As discussed above, the conductive elements in the anisotropic conductor deform under pressure. This ensures that the conductive elements make a robust electrical connection with the contacts (224, FIG. 6A) by increasing the surface area of the interface and allowing the conductive elements to conform to any irregularities or surface texture present in the contacts. Further, at least a portion of the deformation of the conductive elements will be elastic deformation. This elastic deformation exerts a spring force against the contacts that prevents disconnection of the electrical interfaces even if there is a small amount of shifting or other relaxation in other parts of an inline connector.

Figure 10A:
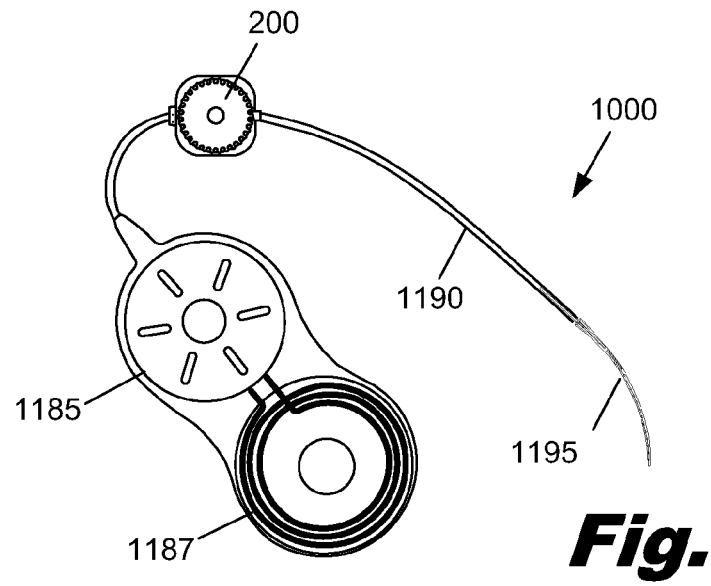
FIGS. 10A and 10B are perspective views of a modular cochlear implant and external components of a cochlear implant system, respectively, according to one embodiment of principles described herein.
Figure 10B:
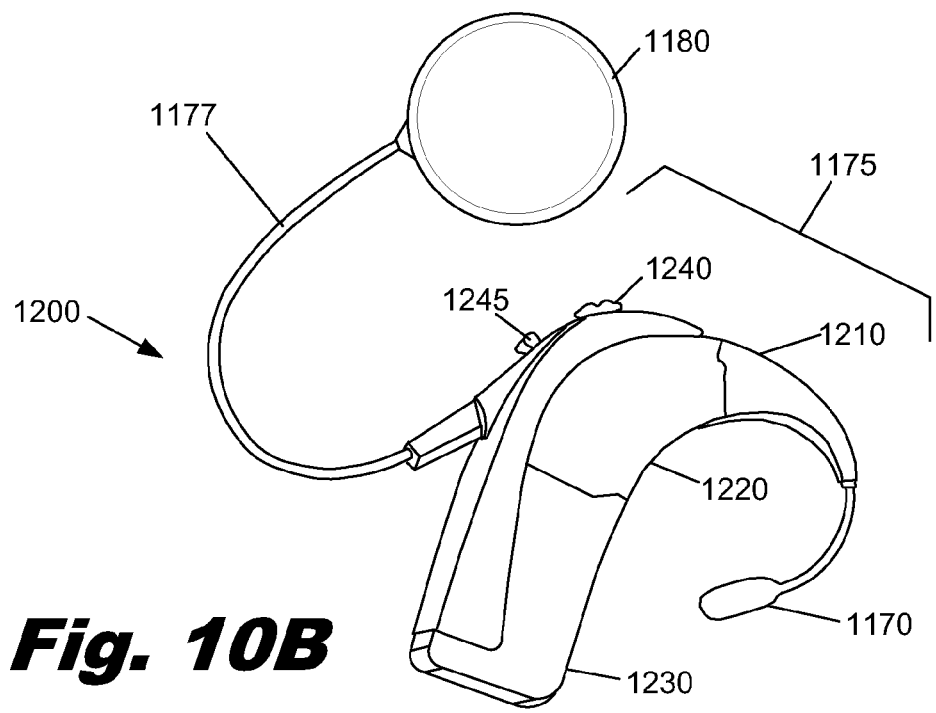
Figure 11:
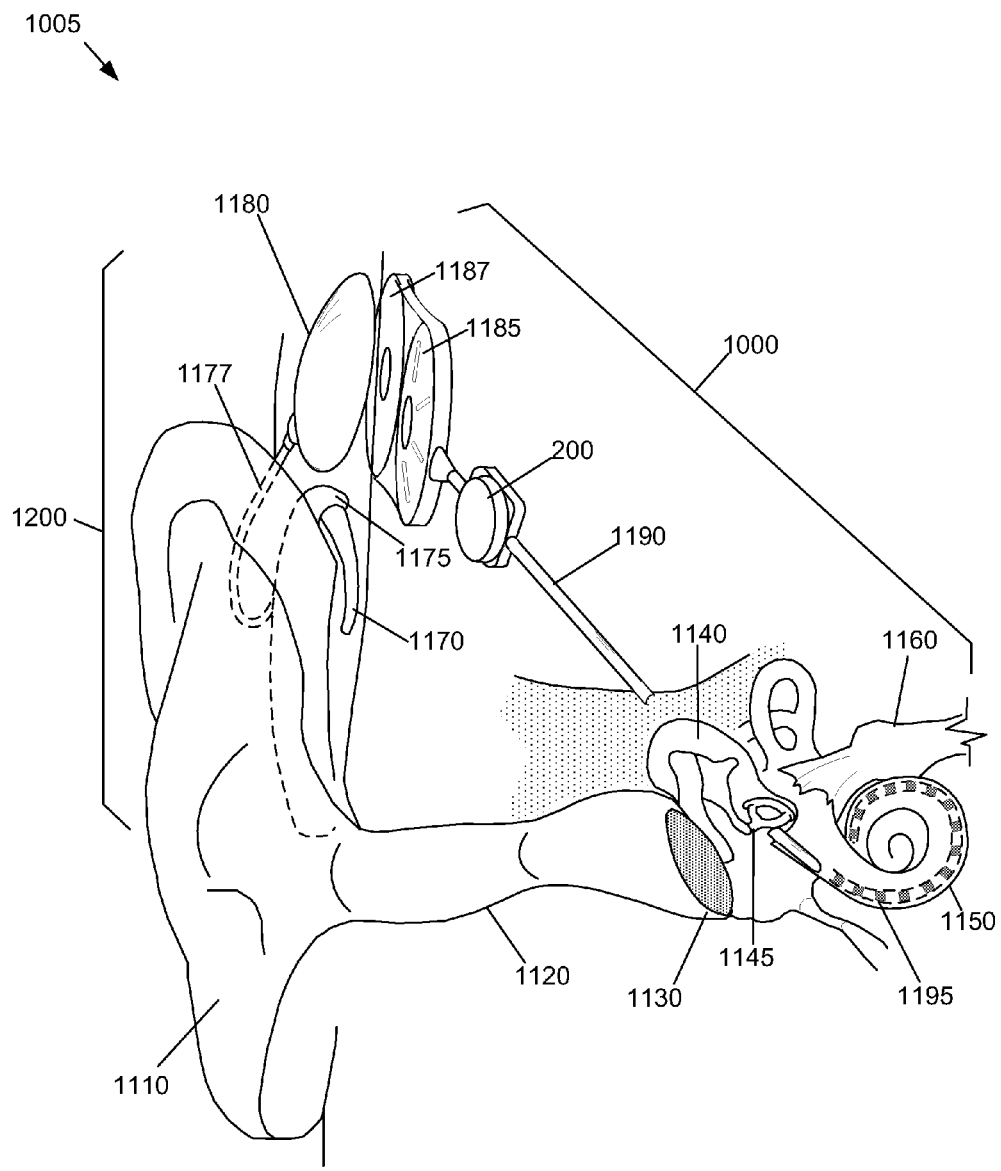
FIG. 11 is a partially cutaway view of a modular cochlear implant surgically positioned within a patient, according to one embodiment of principles described herein.

FIGS. 10A and 10B are perspective views of a modular cochlear implant (1000) and external components (1200) of a cochlear implant system, respectively. FIG. 10A shows the modular cochlear implant (1000) that includes a processor (1185), an antenna (1187), and a cochlear lead (1190) terminating in an electrode array (1195). The cochlear implant (1000) is surgically implanted such that the electrode array (1195) is internal to the patient's cochlea, as shown in FIG. 11 below. The internal processor (1185) and antenna (1187) are secured beneath the user's skin, typically above and behind the external ear with the cochlear lead (1190) connecting the internal processor (1185) to the electrode array (1195) within the cochlea. An inline connector (200) allows the cochlear implant (1000) to be separated into two different assemblies. After separation, the old processor (1185) and old antenna (1187) are removed, and the new cable from a new processor is connected to the electrode array using the inline connector.

FIG. 10B is an illustrative diagram of external portions (1200) of a modular cochlear implant system (1005, FIG. 11) that includes a behind the ear (BTE) unit (1175), that comprises a microphone (1170), an ear hook (1210), a sound processor (1220), and a battery (1230), that may be rechargeable. The microphone (1170) picks up sound from the environment and converts it into electrical impulses. The sound processor (1220) selectively filters and manipulates the electrical impulses and sends the processed electrical signals through a cable (1177) to the transmitter (1180). A number of controls (1240, 1245) adjust the operation of the processor (1220). These controls may include a volume switch (1240) and program selection switch (1245). The transmitter (1180) receives the processed electrical signals from the processor (1220) and transmits these electrical signals and power from the battery (1230) to the cochlear implant (1000, FIG. 10A) by electromagnetic transmission.

The antenna (1187, FIG. 10A) receives signals from the transmitter (1180) and sends the signals to the internal processor (1185, FIG. 10A). The internal processor (1185, FIG. 10A) modifies the signals and passes them along the appropriate wires to activate one or more of the electrodes within the electrode array (1195, FIG. 10A). This provides the user with sensory input that is a representation of external sound waves sensed by the microphone (1170).

FIG. 11 is a partially cutaway view of a modular cochlear implant system (1005). Ordinarily, sound enters the external ear (1110) and is directed into the auditory canal (1120) where the sound wave vibrates the tympanic membrane (1130). The motion of the tympanic membrane (1130) is amplified and transmitted through the ossicular chain (1140), which includes of three bones in the middle ear. The third bone of the ossicular chain (1140), the stapes (1145), contacts the outer surface of the cochlea (1150) and causes movement of the fluid within the cochlea (1150). Cochlear hair cells respond to the fluid-borne vibration in the cochlea (1150) and trigger neural electrical signals that are conducted from the cochlea (1150) to the auditory cortex by the auditory nerve (1160).

As indicated above, the cochlear implant (1000) is a surgically implanted electronic device that provides a sense of sound to a person who is profoundly deaf or severely hard of hearing. The cochlear implant (1000) operates by direct electrical stimulation of the auditory nerve cells, bypassing the defective cochlear hair cells that normally transduce acoustic energy into electrical energy.

As discussed above, external components (1200) of the cochlear implant system can include a Behind-The-Ear (BTE) unit (1175), that contains the sound processor (1220, 10B) and has a microphone (1170), a cable (1177), and a transmitter (1180). The microphone (1170) picks up sound from the environment and converts it into electrical impulses. The sound processor within the BTE unit (1175) selectively filters and manipulates the electrical impulses and sends the processed electrical signals through the cable (1177) to the transmitter (1180). The transmitter (1180) receives the processed electrical signals from the processor and transmits them to the implanted antenna (1187) by electromagnetic transmission.

The components of the cochlear implant (1000) include an internal processor (1185), an antenna (1187), and a cochlear lead (1190) having an electrode array (1195). The internal processor (1185) and antenna (1187) are secured beneath the user's skin, typically above and behind the pinna (1110). The antenna (1187) receives signals and power from the transmitter (1180). The internal processor (1185) receives these signals and performs one or more operations on the signals to generate modified signals. These modified signals are then sent along a number of signal wires that pass through the cochlear lead (1190) and are individually connected to the electrodes in the electrode array (1195). The electrode array (1195) is implanted within the cochlea (1150) and provides electrical stimulation to the auditory nerve (1160).

The cochlear implant (1000) stimulates different portions of the cochlea (1150) according to the frequencies detected by the microphone (1170), just as a normal functioning ear would experience stimulation at different portions of the cochlea depending on the frequency of sound vibrating the liquid within the cochlea (1150). This allows the brain to interpret the frequency of the sound as if the hair cells of the basilar membrane were functioning properly. Severely hard of hearing or deaf patients rely on the cochlear implant to provide sensory input to the cochlea throughout their lifetimes.

As implantable devices progress and in certain types of revision implant surgeries that carry high risk of damaging delicate structures, such as the cochlea, the need for modularizing implantable devices increases. Challenges in designing an implantable electrical connector are numerous. For example, it is desirable for an implantable electrical connector to seal securely, be easy to connect/reconnect in surgical setting, be easy to clean, and have a lifetime of at least 80 years.

An inline connector (200) can be incorporated into a cochlear implant to provide for an easy and safe revision surgery. As discussed above, revision surgery can be desirable for a number of reasons. Electronics continue to improve in terms of decreased size, increased capability, higher reliability, lower noise, and decreased power consumption. Replacing out-dated electronics in implanted devices can provide a number of benefits to the patient including more accurate simulation and greater battery life. Additionally, a modular cochlear implant can make replacement of a processor that failed due to extraordinary circumstances significantly easier and less traumatic to the patient. For example, cranial impacts such as falls and automobile and sporting accidents can cause a portion of the implant, such as the processor, to fail, without necessarily damaging the electrode array. Modularizing the implant improves safety and ease of replacement, since only the damaged portion would be replaced while leaving the electrode array in place. Removing an implanted electrode array from the cochlea and inserting a new electrode array in its place can be difficult because fibrosis can make the cochlear channel narrower. Further, positioning the new electrode array in the cochlea so that its position is identical to the explanted electrode array is challenging. A mismatch in the positions of the old and new electrode arrays would, to some extent, force the patient to relearn speech and sound understanding. Therefore, a revision surgery ideally leaves a functioning electrode array undisturbed and in place in the cochlea.

Figure 12:
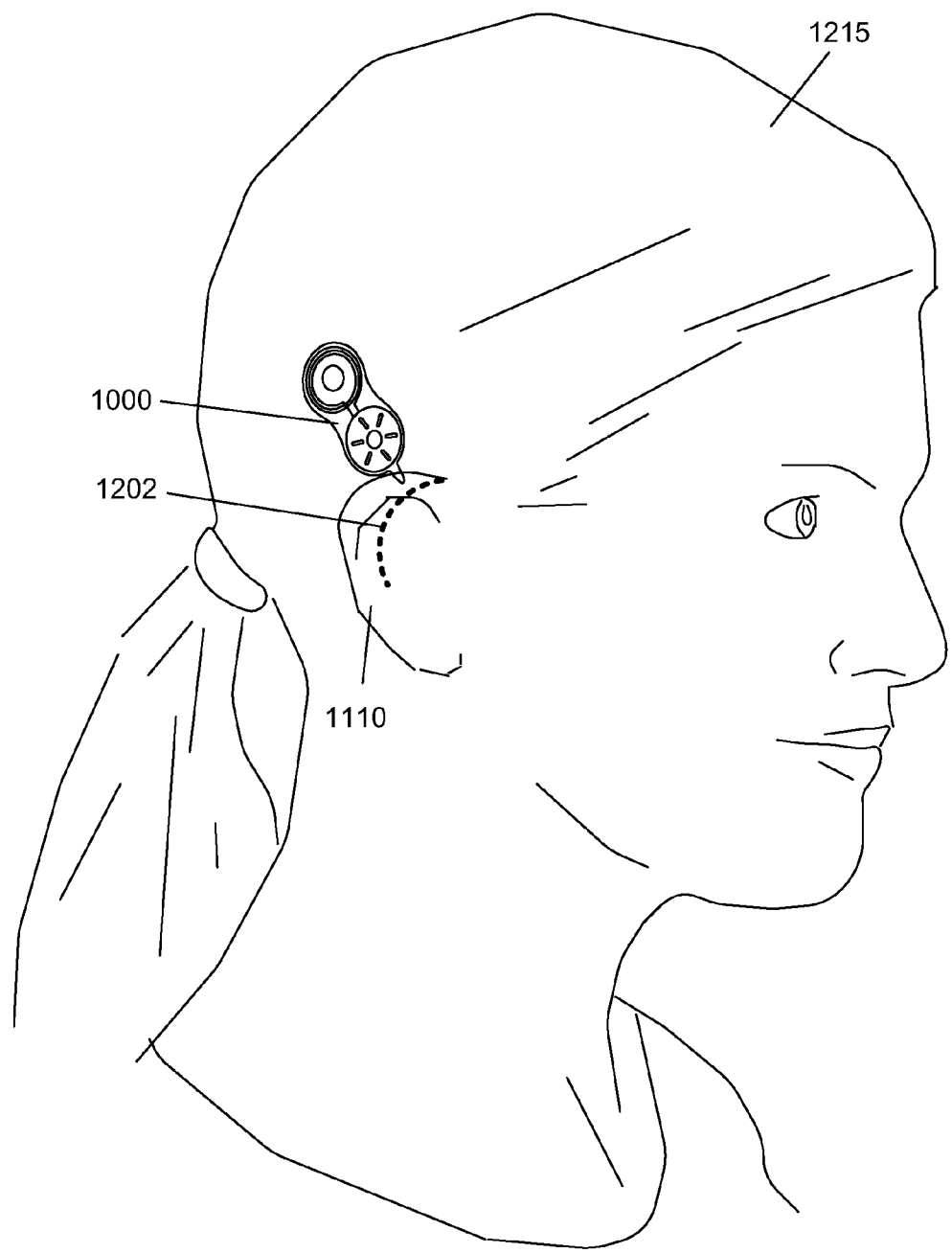
FIG. 12 is a side view of a patient with modular cochlear implant showing the surgical incision used to insert the implant under the patient's skin, according to one example of principles described herein.

FIG. 12 is a side view of a patient (1215) with a modular cochlear implant (1000). The surgical incision (1202) used to insert the implant (1000) under the patient's skin is typically made behind the external ear (1110). Through this incision (1202), additional tissue is removed to access the patient's cochlea and insert the electrode array (1195, 10A). A pocket is made under the skin to receive the antenna and processor. When healed, the incision (1202) is concealed by the external ear (1110).

The embodiments above describe a variety of inline connectors that allow the processor to be replaced. However, a number of other designs could be used to create a modular implant that allows for revision surgery to replace the processor without removing the electrode array.

Figure 13:
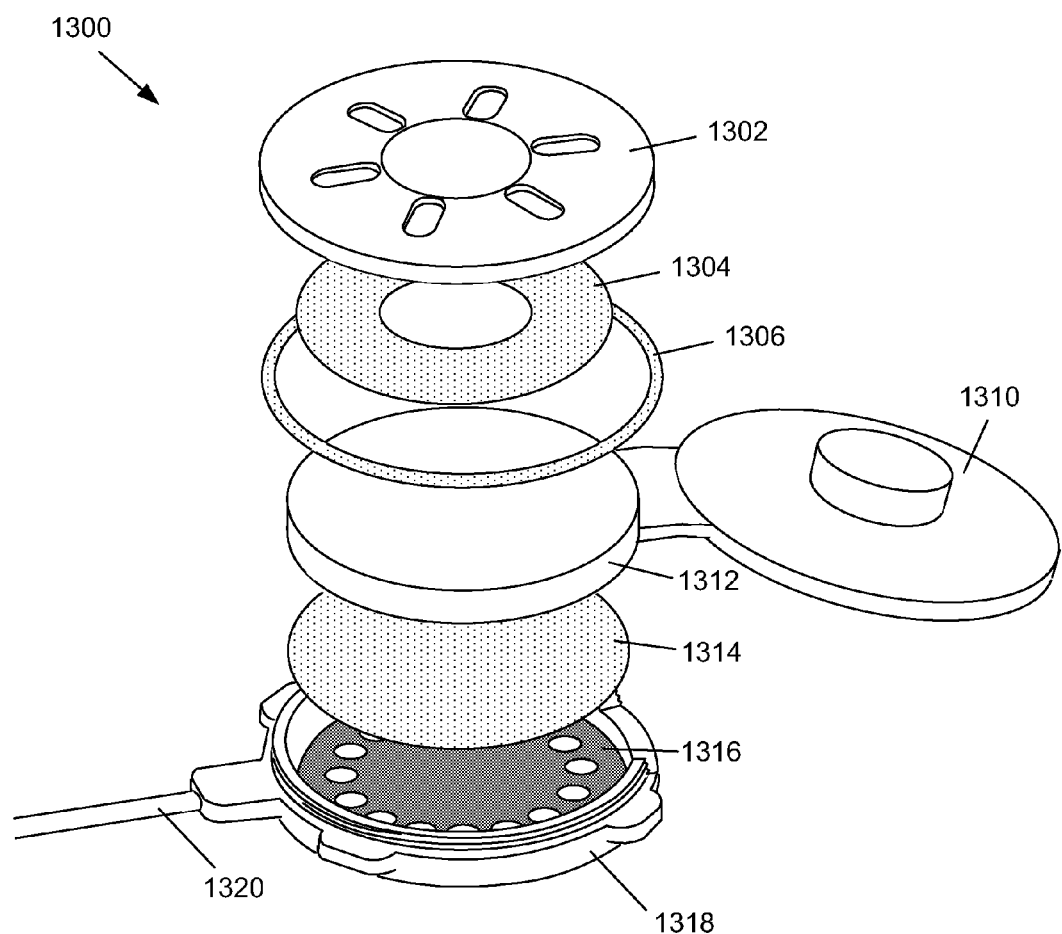
FIG. 13 is an exploded perspective view of a modular cochlear implant that allows a processor, antenna, and anisotropic conductor to be replaced, according to one example of principles described herein.

FIG. 13 is an exploded perspective view of a modular cochlear implant (1300) where the modularity is built into a connection between a processor (1312) and the base (1318). In this example, the processor (1312) is contained within a base (1318) and makes electrical connections with an underlying contact plate (1316) through an anisotropic conductor (1314). The antenna (1310) is hardwired directly connected to the processor (1312). This allows the processor (1312) and antenna (1310) to be replaced as a single unit during a revision surgery.

The cable (1320) to the electrode array terminates in a lower contact plate (1316). The base includes a cavity into which the lower contact plate (1316), anisotropic conductor (1314), and processor (1312) are placed. The lower contact plate (1316) is sealed into the base (1318). A cap (1302) is placed over the processor (1312) and presses it against the anisotropic conductor (1314). A gasket (1306) forms seal around the perimeter of the base (1318). A lubricious spacer (1304) is placed between the upper surface of the processor (1312) and the lower surface of the cap (1302). The lubricious spacer (1304) reduces friction between the upper surface of the processor (1312) and the lower surface of the cap (1302), thereby reducing the force required to screw on or off the cap. The lubricious spacer (1304) also prevents abrasion and undesirable levels of torque from being applied to the processor (1312).

In this example, the processor (1312) is a sealed hermetic can that contains power and signal processing electronics. A hermetic electrical feedthrough on the bottom of the processor (1312) allows for electrical communication with the electrode array.

To replace the processor (1312), antenna (1310), and/or the anisotropic conductor (1314), the cap (1302) is removed and the processor (1312), antenna (1310), anisotropic conductor (1314), gasket (1306), and spacer (1304) are removed. The lower contact plate (1316) can then be inspected and cleaned. The new components can then be placed into the base (1318) in the correct sequence. All of the removable components, including the cap (1302) and gasket (1306) can be replaced if desired. In other implementations, only selected components are replaced.

Figure 14:
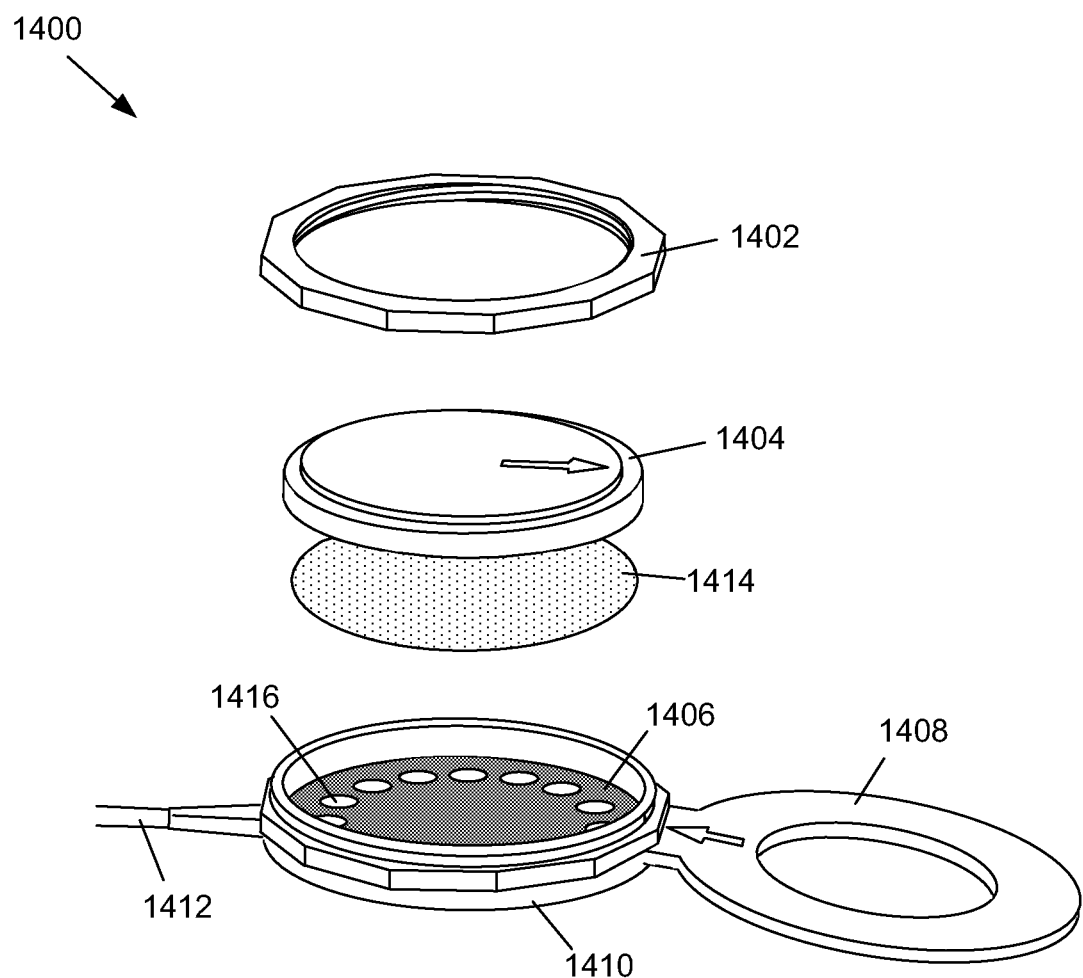
FIG. 14 is an exploded perspective view of a modular cochlear implant that allows a processor and anisotropic conductor to be replaced, according to one example of principles described herein.

FIG. 14 is an exploded perspective view of a modular cochlear implant (1400) that allows a processor (1404) and anisotropic conductor (1414) to be replaced. In this example, the processor (1404) is held into the base (1410) by a ring (1402) that screws over the outside of the base (1410) and fits on a lip of the processor (1404). The cable (1412) to the electrode array terminates in a lower contact plate (1406). The lower contact plate (1406) is integral to the base (1410) and the anisotropic conductor (1414) is placed over it. The processor (1404) includes a hermetic electrical feedthrough with electrical contact pads on its bottom surface. When the ring (1402) presses the processor (1404) against the anisotropic conductor (1414), the pads on the hermetic feedthrough are electrically connected to the contacts (1416) on the lower contact plate (1406). The anisotropic conductor (1414) is resilient and allows for some deflection when the ring (1402) is screwed onto the base (1410).

In this example, the antenna (1408) is hardwired to the base (1410) rather than the processor (1404). The antenna (1408) is electrically connected to contacts (1416) in the lower contact plate (1406). Consequently, the antenna (1408) is not replaced with the processor (1404). Arrows on the processor and antenna provide references to properly align the processor with the base (1410) and the lower contact plate (1406).

Figure 15:
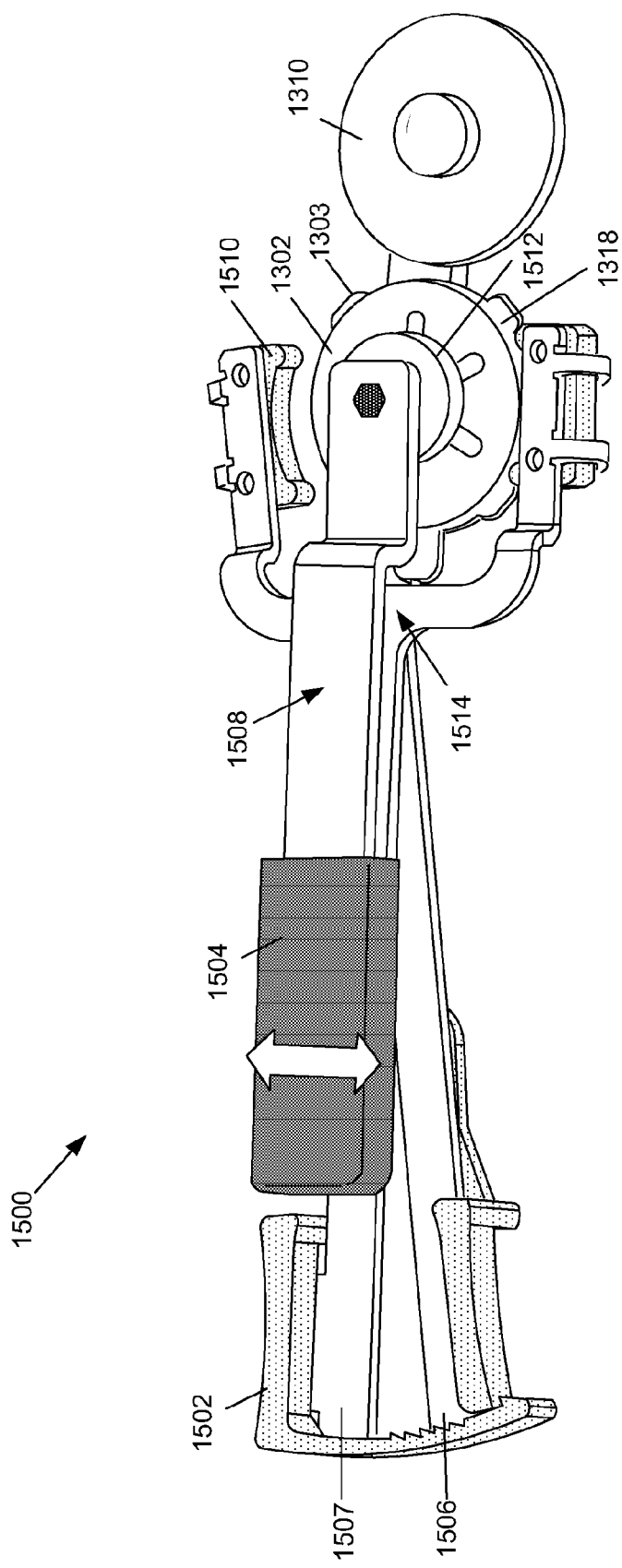
FIG. 15 is a perspective view of an illustrative side access surgical tool for accessing and replacing a processor within a modular cochlear implant, according to one example of principles described herein.

FIG. 15 is a perspective view of an illustrative side access surgical tool (1500) for accessing and replacing a processor (1312, FIG. 13; 1404, FIG. 14) in a modular cochlear implant. The side access surgical tool (1500) includes a gripper tool (1514) with two opposing scissored arms (1506, 1507). The arms (1506, 1507) are connected at a pivot point and terminate in gripper pads (1510) that engage features (1303) on the base (1318). The proximal ends of the arms (1506, 1507) are locked together by a locking mechanism (1502). When the arms (1506, 1507) are squeezed together and locked by the locking mechanism (1502), the gripper pads (1510) on the distal ends of the arms firmly grip the sides of the base (1318).

A separate ratchet mechanism (1508) engages the cap (1302). The ratchet mechanism (1508) includes a handle (1504) and a head (1512). The head (1512) engages the cap (1302) and provides the ratcheting action. By moving the handle (1504) back and forth as shown by the double headed arrow, the cap (1302) can be loosened and removed while the base (1318) is held stationary by the gripper tool (1514). The configuration of the side access surgical tool (1500) accommodates the replacement of a processor (1312, FIG. 13; 1404, FIG. 14) through a surgical opening made in the same place as the original incision. The tissue is raised and tool (1500) is inserted through the opening and around the processor. The advantages of making the revision incision in the same location as the original incision include minimizing scarring and reducing surgical trauma.

Although the side access surgical tool (1500) in this example is configured to facilitate the replacement of the processor by directly opening a cap or ring on attached to the base, the tool could also be designed to open an inline connector (200, FIG. 11). For example, the side access surgical tool (1500) could be used in conjunction with the inline connectors shown in FIG. 2 and FIG. 7.

Figure 16:
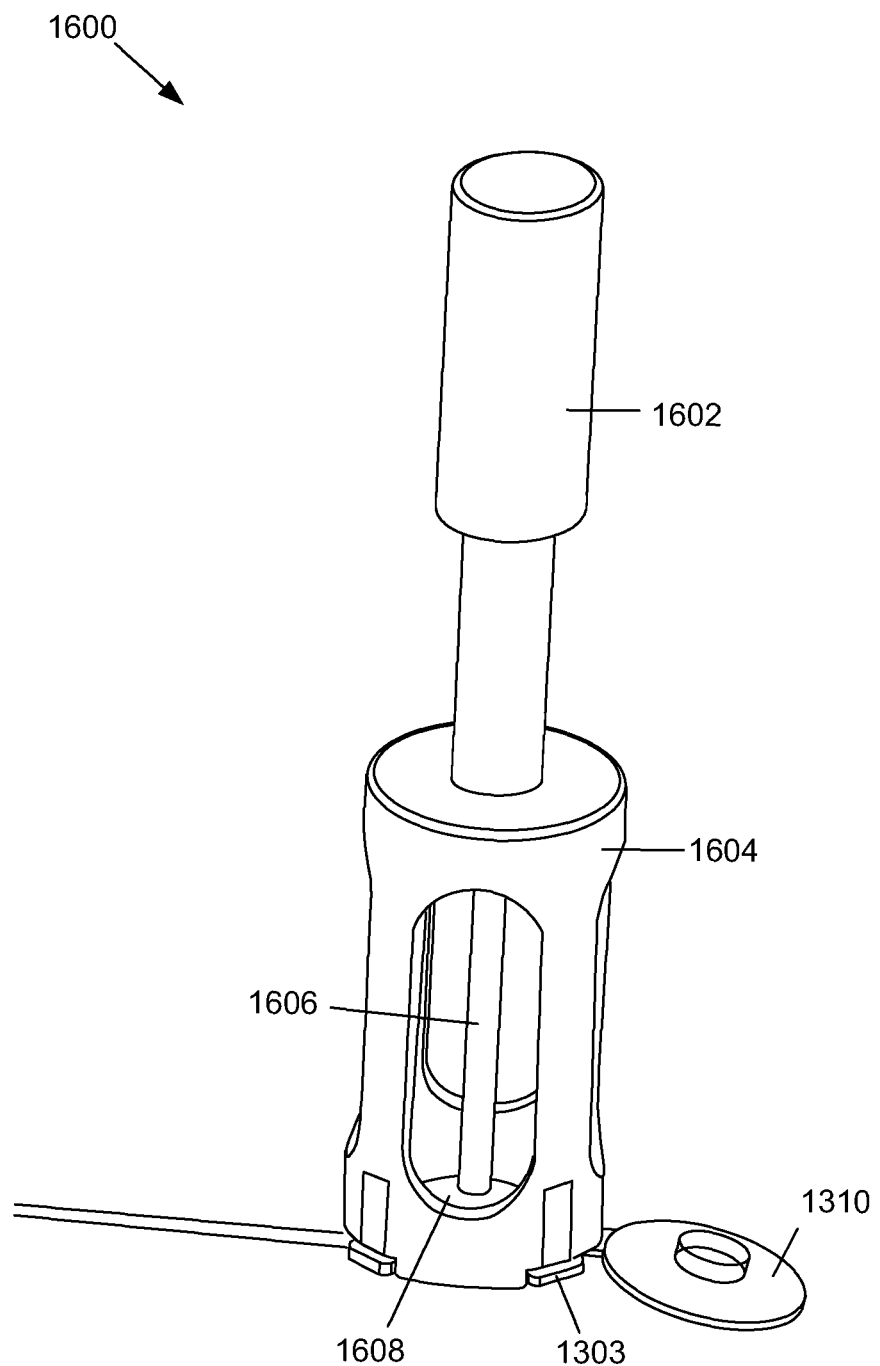
FIG. 16 is a perspective view of an illustrative top access surgical tool for accessing and replacing a processor within a modular cochlear implant, according to one example of principles described herein.

FIG. 16 is a perspective view of an illustrative top access surgical tool (1600) for accessing and replacing a processor (1312, FIG. 13; 1404, FIG. 14) within a modular cochlear implant (1300, FIG. 13; 1400, FIG. 14). Where the cochlear implant was originally inserted through a surgical opening (1202, FIG. 12) just behind the ear, an additional incision may be made to expose the upper surface of the cochlear implant (1300, FIG. 13; 1400, FIG. 14). This incision may be made midline of the processor. This provides direct vertical access to the cap (1302, FIG. 13; 1402, FIG. 14) and base (1318, FIG. 13; 1410, FIG. 14). The top access surgical tool (1600) includes a gripper portion (1604) that fits around the perimeter of the base and holds the base stationary by engaging features (1303) on the base. These features (1303) may be any type of slot, protrusion, flat or other geometry that allows the gripper portion (1604) to engage with the base and control the rotational movement of the base. The top access surgical tool (1600) also includes a torque driver made up of a torque limiting handle (1602), a shaft (1606), and an engagement portion (1608). The engagement portion (1608) engages with the cap, ring, or other locking mechanism. The torque limiting handle (1602) is turned by the surgeon to create torque which is passed through the shaft (1606) to the engagement portion (1608). The engagement portion (1608) rotates the cap (1302, FIG. 13; 1402, FIG. 14) to remove or tighten the cap on the base.

During a replacement procedure, the cap (1302, FIG. 13; 1402, FIG. 14) is screwed off the base (1318, FIG. 13; 1410, FIG. 14) and the processor (1312, FIG. 13; 1404, FIG. 14) and anisotropic conductor (1314, FIG. 13; 1414, FIG. 14) are removed. The midline incision allows for direct exposure, inspection, and cleaning of the base (1318, FIG. 13; 1410, FIG. 14) and lower contacts (1416, FIG. 14). A new processor and a new anisotropic conductor are placed in the base, and the cap is screwed back into place. As discussed above, this compresses the anisotropic conductor between the processor and the lower contact plate to form an electrical connection between pads on the lower surface of the processor and the lower contacts (1416, FIG. 14). The top access surgical tool (1600) in this example can also be configured to remove and replace a cap on an inline connector (262, FIG. 8; 200, FIG. 11).

Figure 17:
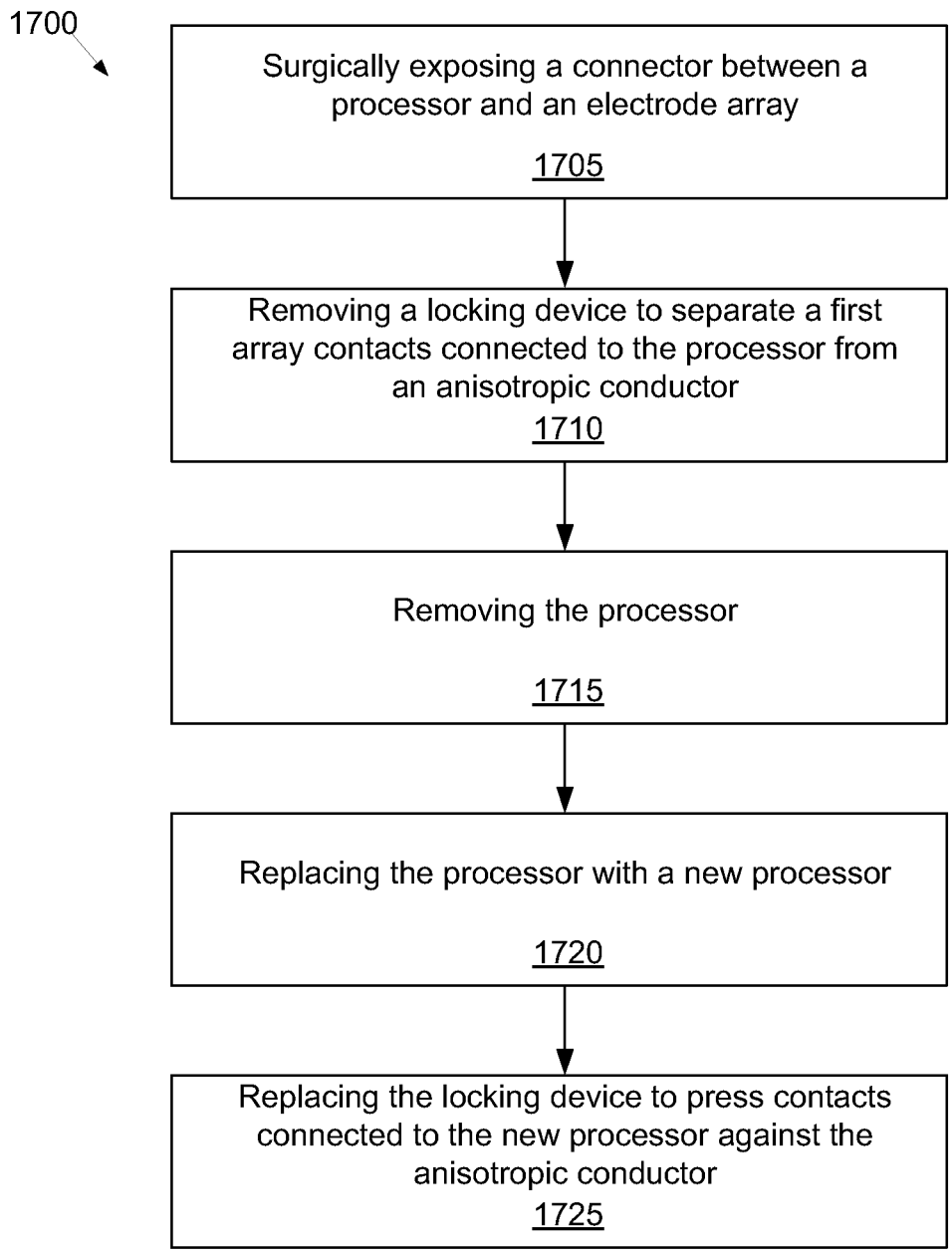
FIG. 17 is a flowchart showing an illustrative method for replacing a processor and anisotropic conductor in a modular biomedical implant, according to one example of principles described herein.

FIG. 17 is a flowchart of illustrative method (1700) for replacing a processor and anisotropic conductor in a modular biomedical implant. The method includes surgically exposing a connector between a processor and an electrode array (step 1705). The connector may be an inline connector such as those illustrated in FIGS. 2-9 or a base that receives the processor as illustrated in FIGS. 13 and 14. A locking device, such as a cap, ring, snap ring, latch, or other appropriate device is removed to separate a first array contacts connected to the processor from an anisotropic conductor (step 1710). The first array of contacts may be an upper contact plate as illustrated in FIGS. 2, 3, and 4C or may be pads on a hermetic electrical feedthrough in the processor as described with reference to FIGS. 13 and 14. The anisotropic conductor may be formed any of a number of materials, including an anisotropic conductive elastomer, an array of conductive balls disposed in an elastomeric matrix, or other element that exhibits significantly greater conduction through its thickness than in lateral directions. The anisotropic element is sandwiched between the first array of contacts and a second array of contacts connected to the electrode array.

The processor is removed (step 1715). A number of other elements may also be removed and replaced, such as the anisotropic conductor, gaskets, upper contact plate, cap, overcoat, locking device or other elements. The processor is replaced with a new processor (step 1720). The locking device is replaced and presses contacts connected to the new processor against the anisotropic conductor (step 1725). The anisotropic conductor deforms under the pressure exerted by the locking device.

In conclusion, a modular implanted device can provide a number of advantages, including reducing costs and risks in explanting/repairing the modular device. Where the modular implanted device includes an electrode array, the modularity of the implanted device allows the electrode array to remain in place while the processor and other components are replaced. This mitigates nerve and other tissue damage and eliminates the need for the patient to relearn a new pattern of sensory input.

The preceding description has been presented only to illustrate and describe examples of the principles described. This description is not intended to be exhaustive or to limit these principles to any precise form disclosed. Many modifications and variations are possible in light of the above teaching.

What is claimed is:

1. A modular biomedical implant comprising:
a processor;
an electrode array;
a cable, a first end of the cable attached to the electrode array and a second end of the cable terminating in a first array of contacts;
a second array of contacts electrically connected to the processor;
a separate anisotropic conductor disposed between the first array of contacts and the second array of contacts, the anisotropic conductor forming electrical connections between the first array of contacts and the second array of contacts; and
a compression spring configured to press the second array of contacts against the anisotropic conductor.

2. The implant of claim 1, further comprising a compression plate overlying the anisotropic conductor, in which the compression spring is compressed by screwing a cap onto a base.

3. A modular biomedical implant comprising:
a processor:
an electrode array;
a cable, a first end of the cable attached to the electrode array and a second end of the cable terminating in a first array of contacts:
a second array of contacts electrically connected to the processor: and
a separate anisotropic conductor disposed between the first array of contacts and the second array of contacts, the anisotropic conductor forming electrical connections between the first array of contacts and the second array of contacts:
in which the processor is retained within a base by a snap ring.

4. A method for replacing a processor of a modular biomedical device comprising a processor; an electrode array; a cable, a first end of the cable attached to the electrode array and a second end of the cable terminating in a first array of contacts; a second array of contacts electrically connected to the processor; and a separate anisotropic conductor disposed between the first array of contacts and the second array of contacts, the anisotropic conductor forming electrical connections between the first array of contacts and the second array of contacts, the method comprising:
surgically exposing a connector between the processor and the electrode array;
removing a locking device of the connector to separate the second array of contacts connected to the processor from the anisotropic conductor;
removing the processor and the anisotropic conductor;
replacing the processor with a new processor and a new anisotropic conductor;
and replacing the locking device to press the second array of contacts connected to the new processor against the new anisotropic conductor.

5. The method of claim 4, in which removing the processor further comprises removing an antenna.

6. The method of claim 4, in which removing a locking device comprises:
grasping a base of the connector on two opposing sides with a surgical tool to hold the base stationary; and
grasping a cap of the connector with the surgical tool and rotating the cap with the surgical tool while holding the base stationary.

7. The method of claim 6, in which surgically exposing the connector comprises reopening a original incision; the surgical tool being inserted horizontally into the original incision and grasping the base and cap from the side.

8. The method of claim 6, in which surgically exposing the connector comprises making a new incision midline of the modular biomedical device and inserting the surgical tool vertically through the new incision to access the base and cap from the top.

9. A modular biomedical implant comprising:
a processor;
an electrode array:
a cable, a first end of the cable attached to the electrode array and a second end of the cable terminating in a first array of contacts:
a second array of contacts electrically connected to the processor: and
a separate anisotropic conductor disposed between the first array of contacts and the second array of contacts, the anisotropic conductor forming electrical connections between the first array of contacts and the second array of contacts:
wherein the anisotropic conductor is configured to conduct electricity through a thickness of the anisotropic conductor between the first array of contacts and the second array of contacts, but to not conduct electricity laterally to an axis running between the first array of contacts and the second array of contacts.

* * * * *